US008349813B2

(12) United States Patent
Johnson et al.

(10) Patent No.: US 8,349,813 B2
(45) Date of Patent: Jan. 8, 2013

(54) DESTRUCTION OF MICROBIAL PRODUCTS BY ENZYMATIC DIGESTION

(75) Inventors: Richard J. Johnson, Mundelein, IL (US); Valerie Leesch, Buffalo Grove, IL (US); Clifford Holmes, Glenview, IL (US); Run Wang, Gurnee, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 671 days.

(21) Appl. No.: 12/407,516

(22) Filed: Mar. 19, 2009

(65) Prior Publication Data

US 2009/0239821 A1 Sep. 24, 2009

Related U.S. Application Data

(60) Provisional application No. 61/038,297, filed on Mar. 20, 2008.

(51) Int. Cl.
*A61K 31/715* (2006.01)
*C12Q 1/00* (2006.01)

(52) U.S. Cl. ............................ 514/54; 435/4; 435/262

(58) Field of Classification Search .............. 435/4, 262; 514/54

See application file for complete search history.

(56) References Cited

U.S. PATENT DOCUMENTS

| | | | |
|---|---|---|---|
| 3,669,878 | A | 6/1972 | Marantz et al. |
| 3,669,880 | A | 6/1972 | Marantz et al. |
| 3,707,967 | A | 1/1973 | Kitrilakis et al. |
| 3,884,808 | A | 5/1975 | Scott |
| 4,303,521 | A | 12/1981 | Lussling et al. |
| 4,313,831 | A | 2/1982 | Lehmann et al. |
| 4,364,747 | A | 12/1982 | Blackshear, Jr. |
| 4,386,611 | A | 6/1983 | Kantorski et al. |
| 4,460,555 | A | 7/1984 | Thompson |
| 4,542,015 | A | 9/1985 | Smakman et al. |
| 4,610,791 | A | 9/1986 | Henne et al. |
| 4,650,587 | A | 3/1987 | Polak et al. |
| 4,659,744 | A | 4/1987 | Matsui et al. |
| 4,661,246 | A | 4/1987 | Ash |
| 4,721,652 | A | 1/1988 | Takai et al. |
| 4,765,907 | A | 8/1988 | Scott |
| 4,806,244 | A | 2/1989 | Guilhem |
| 4,988,569 | A | 1/1991 | Okazaki et al. |
| 5,277,820 | A | 1/1994 | Ash |
| 5,514,281 | A | 5/1996 | Boos et al. |
| 5,536,412 | A | 7/1996 | Ash |
| 5,618,441 | A | 4/1997 | Rosa et al. |
| 5,618,710 | A | 4/1997 | Navia et al. |
| 5,744,042 | A | 4/1998 | Stange et al. |
| 5,919,369 | A | 7/1999 | Ash |
| 5,944,684 | A | 8/1999 | Roberts et al. |
| 6,309,673 | B1 | 10/2001 | Duponchelle et al. |
| 6,627,164 | B1 | 9/2003 | Wong |
| 7,118,857 | B2 | 10/2006 | Martis et al. |
| 2004/0229771 | A1* | 11/2004 | Deppisch et al. ................ 514/1 |
| 2005/0191717 | A1 | 9/2005 | Martis et al. |

FOREIGN PATENT DOCUMENTS

| | | |
|---|---|---|
| DE | 196 40 841 | 5/1998 |
| EP | 0 003 914 | 9/1979 |
| EP | 0 064 393 | 11/1982 |
| EP | 0 207 676 | 1/1987 |
| GB | 2 122 509 | 1/1984 |
| GB | 2 124 511 | 2/1984 |
| WO | 95/02559 | 1/1995 |

OTHER PUBLICATIONS

Millar et al. International Congress Series (2002), 1245 (Maillard Reaction in Food Chemistry and Medical Science) 475-477; Abstract.*
Millar et al.International Congress Series (2002), 1245(Maillard Reaction in Food Chemistry and Medical Science), 487-489; abstract.*
F. Toure et al., "Icodextrin-induced peritonitis: Study of five cases and comparison with bacterial peritonitis" Kidney Inter. Nature Publishing Group—Feb. 1, 2004—vol. 65, No. 2, pp. 654-660.
Search Report for International Application No. WO 2009/117558—Jun. 4, 2010.
White, D "Peptidoglycan of Myxococcus xanthus: Structure and Relation to Morphogenesis", Journal of Bacteriology—Jun. 1968—vol. 95, No. 6, p. 2186-2197, USA.
Amano, K "Sensitivity of *Coxiella burnetii* peptidoglycan to lysozyme hydrolysis and correlation of sacculus rigidity with peptidoglycan-associated proteins", Journal of Bacteriology—Dec. 1984—vol. 160, No. 3, p. 989-993, USA.
Janusz, M. J. "In Vivo Degradation of Bacterial Cell Wall by the Muralytic Enzyme Mutanolysin", Infection and Immunity—May 1986—vol. 52, No. 2, p. 459-467, USA.
Takada, K "Lysozyme Regulates LPS-Induced Interleukin-6 Release in Mice", Circulatory Shock—Dec. 1994—vol. 44, p. 169-174.
Hoijer, M.A. "Expression and Intracellular Localization of the Human N-acetylmuramyl-L-alanine Amidase, a Bacterial Cell Wall-Degrading Enzyme", Blood—Apr. 1997—vol. 90, p. 1246-1254, USA.
Hoijer, M.A. "Inflammatory Properties of Peptidoglycan are Decreased After Degradation by Human N-acetylmuramyl-L-alanine Amidase", Eur. Cytokine Netw.—Dec. 1997—vol. 8, No. 4, p. 375-382.
Majcherczyk, P.A. "Digestion of *Streptococcus pneumonia* Cell Walls with Its Major Peptidoglycan Hydrolase Releases Branched Stem Peptides Carrying Proinflammatory Activity", J. of Biological Chemistry—Apr. 30, 1999—vol. 274, No. 18, p. 12537-12543, USA.
Myhre, A "Organ Injury and Cytokine Release Caused by Peptidoglycan Are Dependent on the Structural Integrity of the Glycan Chain", Infection and Immunity—Mar. 2004—vol. 72, No. 3, p. 1311-1317, USA.
Bochtler, M "Similar Active Sites in Lysostaphins and D-Ala-D-Ala Metallopeptidases", Protein Science—2004—vol. 13, p. 854-861.

* cited by examiner

*Primary Examiner* — Chih-Min Kam
(74) *Attorney, Agent, or Firm* — K&L Gates LLP

(57) ABSTRACT

Methods of treating a dialysis component by providing a dialysis component and contacting the dialysis component with an enzyme are provided. The enzyme breaks down microbial contaminants in the dialysis component. The enzyme may be separated from the dialysis component to provide a purified dialysis component. The purified dialysis component may be substantially free of microbial contaminants that cause a cytokine response in humans.

21 Claims, 3 Drawing Sheets

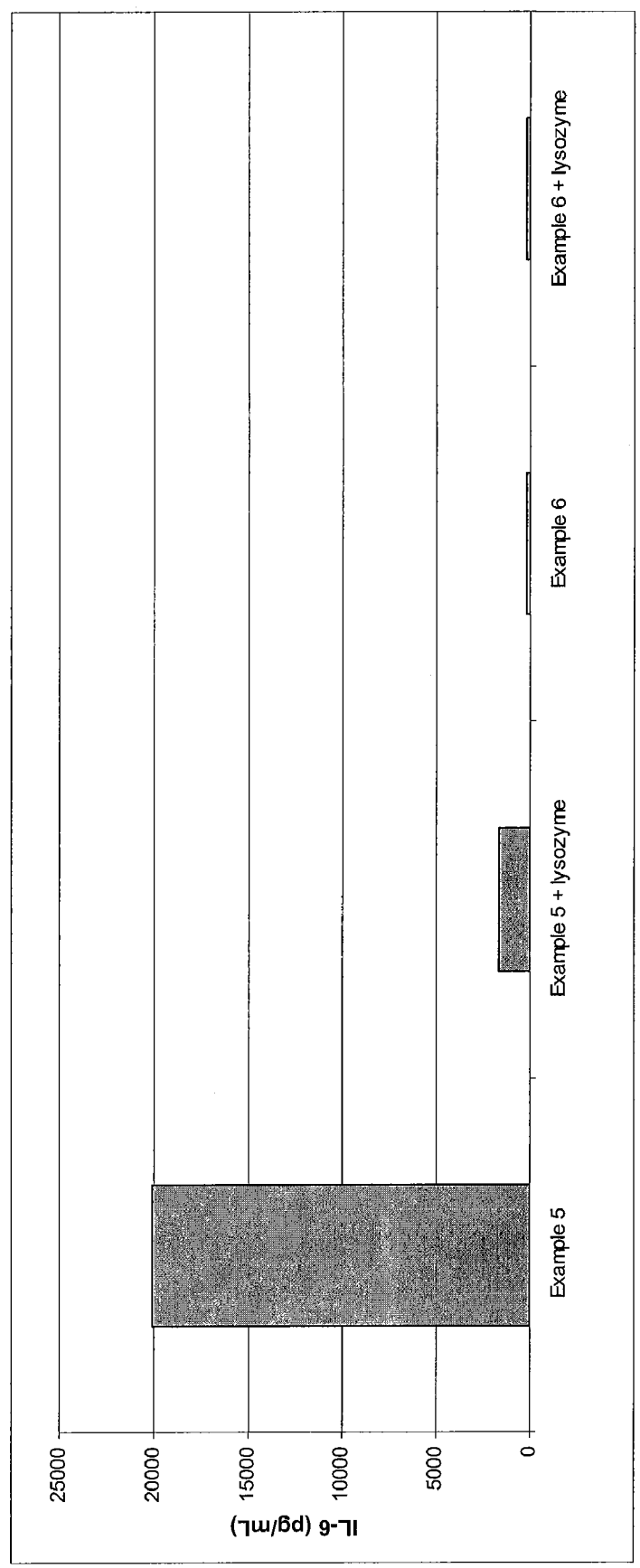

2

DESTRUCTION OF MICROBIAL PRODUCTS BY ENZYMATIC DIGESTION

PRIORITY CLAIM

This application claims the benefit of U.S. Provisional Patent Application Ser. No. 61/038,297 filed Mar. 20, 2008, the entire disclosure of which is expressly incorporated herein by reference.

BACKGROUND

The present disclosure relates generally to methods of removing contaminants from dialysis components. More particularly, the present disclosure relates to methods of destroying microbial products in a dialysis solution, or in the components used to make a dialysis solution, by enzymatic digestion, and methods of using the purified dialysis solution or component thereof.

Parenteral pharmaceutical products are required to be free of contaminating substances, such as those that might cause peritonitis. Peritonitis, or inflammation of the peritoneum, is a major complication of peritoneal dialysis. Peritonitis may be caused by intraperitoneal bacterial infections. Alternatively, peritonitis caused by a chemical or a foreign body irritant is known as aseptic or sterile peritonitis. Sterile peritonitis is accompanied with development of a cloudy dialysate. Despite existing testing of peritoneal dialysis solutions, outbreaks of aseptic peritonitis still occur.

SUMMARY

The present disclosure relates to methods of removing bacterial contaminants from dialysis components and of using dialysis solutions made from the components. In an general embodiment, the present disclosure provides a method of treating a dialysis component. The method comprises providing a dialysis component and contacting the dialysis component with one or more enzymes. The enzyme(s) breaks down microbial contaminants in the dialysis component. The enzyme(s) may be separated from the dialysis component to provide a purified dialysis component. The purified dialysis component may be substantially free of microbial contaminants that cause a cytokine response in humans.

In an embodiment, the dialysis component is an osmotic agent. For example, the osmotic agent can be glucose, fructose, glucose polymers, glucose polymer derivatives, polyols, amino acids, peptides, proteins, amino sugars, N-acetyl glucosamine (NAG), glycerol or combinations thereof. In alternative embodiments, the dialysis component is one or more buffers or electrolytes used in dialysis treatments.

In an embodiment, the enzyme can be one or more of lysozymes, amidases, trypsins, chitinases, beta 1-3 glucanases, pronases, proteases, lipases and endoglycosidases. The enzyme may also be N-acetylmuramyl-L-alanine amidase. The enzyme may be added at a ratio of between about 0.0005% and about 0.05% by weight of the dialysis component. The dialysis component and the enzyme may be incubated for a period of time. The period of time may be at least 1 hour or longer.

In an embodiment, the step of contacting the dialysis component with an enzyme includes adding to the dialysis component a treatment solution containing the enzyme. The step of separating the enzyme from the dialysis component may include filtering the enzyme from the dialysis component. The enzyme may be either naturally larger than the molecular weight cut off of the filter, or the enzyme may be modified to increase its molecular weight.

In another embodiment, the enzyme is fixed to a substrate. The substrate may be a bead or a membrane. The substrate may be part of a cartridge or dialyzer used in dialysis systems and treatments.

In an embodiment, the step of contacting the dialysis component with an enzyme is performed in a batch process. The step of contacting the dialysis component with an enzyme may also be performed in a continuous process.

In an embodiment, the dialysis component is tested for the presence of microbial contaminants after the step of allowing the enzyme to break down microbial contaminants in the dialysis component. The testing may be interleukin-6 testing.

In an embodiment, the dialysis component includes peptidoglycan as a microbial contaminant. The dialysis component may be icodextrin.

In an embodiment, the present disclosure provides a method of treating a peritoneal dialysis solution comprising providing a peritoneal dialysis solution. The peritoneal dialysis solution includes an osmotic agent such as a glucose polymer or a glucose polymer derivative. The peritoneal dialysis solution is contacted with an enzyme. The enzyme is allowed to break down microbial contaminants in the peritoneal dialysis solution.

In another embodiment, the present disclosure provides a method of providing peritoneal dialysis solution to a patient. The method comprises providing a peritoneal dialysis component and contacting the peritoneal dialysis component with an enzyme. The enzyme is allowed to break down microbial contaminants in the peritoneal dialysis component. The peritoneal dialysis solution is used in the dialysis treatment of a patient.

An advantage of the present disclosure is to provide improved methods for removing a substance from dialysis solutions and/or dialysis components.

Another advantage of the present disclosure is to provide improved methods for manufacturing dialysis solutions or components used to make dialysis solutions.

Yet another advantage of the present disclosure is to provide improved dialysis solutions.

Still another advantage of the present disclosure is to provide improved safety procedures that can be employed to prevent peritonitis in patients that receive peritoneal dialysis therapy.

Another advantage of the present disclosure is to provide improved methods for administering dialysis solutions to a patient.

Additional features and advantages are described herein, and will be apparent from the following Detailed Description and the figures.

BRIEF DESCRIPTION OF THE FIGURES

FIG. 3 is a chart illustrating the interleukin-6 response for test samples of icodextrin solutions before and after enzymatic treatment and filtering.

DETAILED DESCRIPTION

Figure 1:
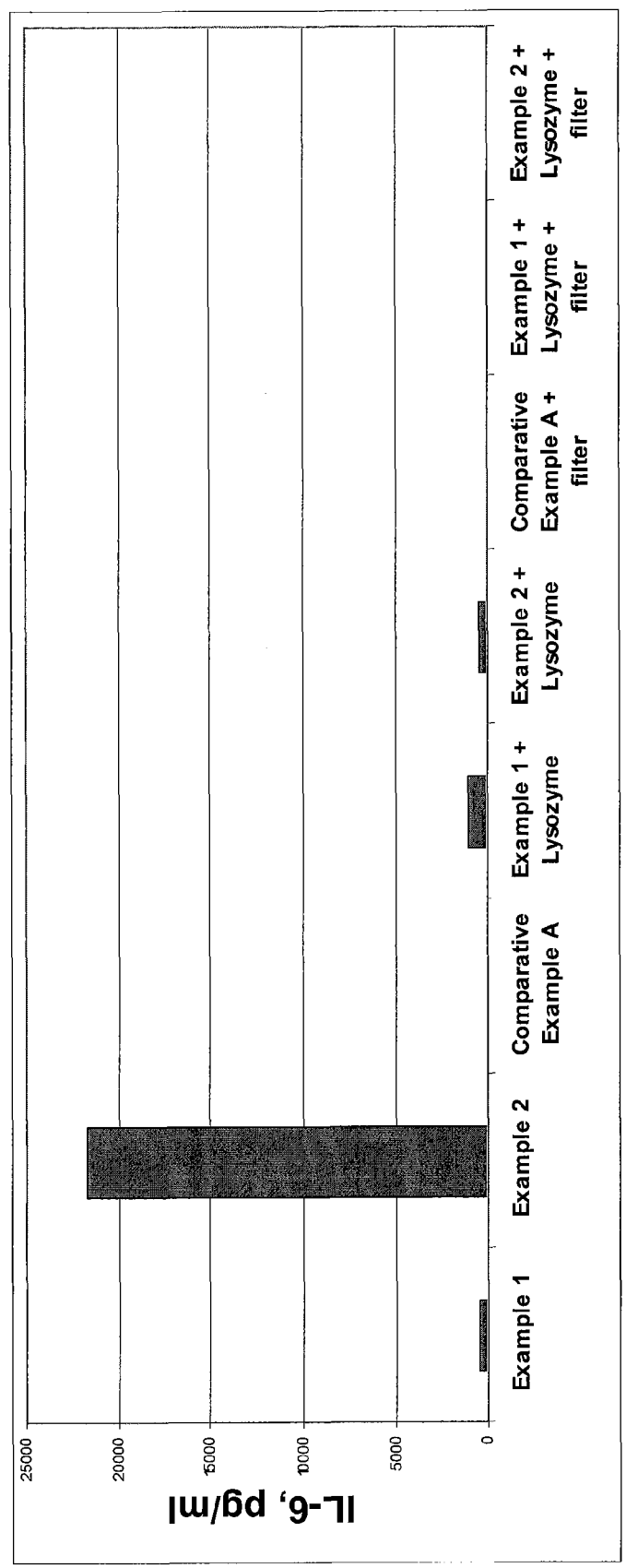
FIG. 1 is a chart illustrating the interleukin-6 response for test samples of dialysis solutions before and after enzymatic treatment and filtering.

The present disclosure relates to methods of using an enzyme to break down bacterial components in a dialysis component. Dialysis solutions are used in various forms of dialysis to remove waste products from a patient. Dialysis solutions can be specifically formulated and suitable for peritoneal dialysis, hemodialysis or any other dialysis therapies. The dialysis solutions can include one or more suitable dialysis components (e.g. ingredients or constituents of a dialysis solution) such as osmotic agents, buffers, electrolytes or combinations thereof. The methods disclosed herein may be used with any type of dialysis components or any type of dialysis solution.

Various compounds that are major components of a bacterial cell wall can serve as a marker for bacteria. Many of these microbial products, including lipopolysaccharide ("LPS") and peptidoglycan ("PG"), stimulate cytokine production in human cells. These microbial products may provoke unacceptable reactions in a patient, including peritonitis. It has been found that enzymes can feasibly degrade these microbial products into harmless by-products so that they do not provoke a cytokine response.

To destroy the microbial products, a dialysis component is contacted with one or more enzymes. The dialysis component may be provided in solution form. The enzyme break downs or digests microbial contaminants in the dialysis component. The enzyme is separated from the dialysis component to provide a purified dialysis component. The purified dialysis component may be substantially free of microbial contaminants that cause a cytokine response. Thus, the treatment of the dialysis component with an enzyme destroys microbial contaminants (such as peptidoglycan) and ensures these inflammatory agents are not carried through to the final dialysis product.

The enzyme can be selected to break molecular bonds in the bacterial components to break down the components into harmless compounds. For example, lysozyme (also known as muramidase) is a 14.4 kDa enzyme that catalyzes hydrolysis of 1,4-beta-linkages between N-acetylmuramic acid and N-acetyl-D-glucosamine residues in peptidoglycan. Amidase is an enzyme that catalyzes the hydrolysis of monocarboxylic amides. Trypsin is a serine protease that breaks down proteins by cleaving peptide chains. N-acetylmuramyl-L-alanine amidase can also be used to degrade peptidoglycan. Chitinase can degrade chitin, a fungal cell wall polysaccharide. Beta 1-3 glucanase can likewise be used to degrade microbial cell wall polysaccharides such as curdlan and zymosan. Other possible enzymes include pronase, other proteases, lipases and endoglycosidases.

The dialysis component can be exposed to the enzyme by any suitable techniques. The enzyme may be prepared in a solution and then added to the dialysis component or solution thereof. Alternatively, the enzyme may be fixed to a substrate such as a bead or filter. For example, the dialysis component may be percolated through a column where the enzyme has been immobilized.

The enzyme may be added to the dialysis component at a ratio of between about 0.000005% to about 0.5%, preferably between about 0.0005% to about 0.05%, by weight of the dialysis component. For example, a treatment solution including 1 mg/mL of enzyme may be prepared in water. The treatment solution is then added to the dialysis component at a ratio of about 1%. The dialysis component and the treatment solution are allowed to incubate for a period of between one to five hours, with three hours a typical period.

After the incubation period, the enzyme is removed from the dialysis component. In one embodiment, the solution may be filtered to remove the enzyme. The filtration may be performed by any suitable filtration technique. In one embodiment, the enzyme has a molecular weight larger than the largest dialysis component of the dialysis solution (e.g. a glucose polymer or glucose polymer derivative), or above 50 kDa. In another embodiment, the enzyme (such as lysozyme, which has a molecular weight of 14 kDa) may be attached to a larger carrier molecule that increases its nominal molecular weight, such as polyethylene glycol polymers that can be attached to the lysozyme protein. The filter unit may include a molecular weight cutoff designated as the nominal molecular weight limit ("NMWL"). The molecular weight cutoff indicates the ability of the device to retain molecules above the specified molecular weight. The NMWL used may be 30 kDa. Other filtration methods, such as carbon filtration, may also be used.

In another embodiment, the enzyme is fixed to a substrate. The substrate may be part of a cartridge or dialyzer used in dialysis systems and treatments. The enzyme may be covalently attached to beads and the dialysis solution exposed to the beads in a batch process. Alternatively, the dialysis component may be percolated through a column where the enzyme has been immobilized to a substrate or matrix. The substrate may be a bead, a membrane, or any other suitable substrate. By attaching the enzyme to a substrate, a process to filter or otherwise remove the enzyme from the dialysis solution may not be necessary. Additionally, the enzyme may be used multiple times, lowering the cost of the treatment step.

After the treatment step, the dialysis component may be tested to confirm the absence of contaminants likely to cause peritonitis. The cytokine response induced by a material may be measured. One suitable cytokine response that has been found useful for detecting the presence of microbial contaminants is the interleukin-6 response. In one type of test, a reagent that produces a cytokine response is added to a sample of the dialysis component. The reagent may include peripheral blood mononuclear cells ("PBMCs") or monocytic cell line cells. PBMCs are isolated from fresh human blood of healthy donors. One particular type of suitable test includes a test kit with an assay. The material to be tested and PBMCs are added to the assay. The assays are then incubated with the cells overnight. The culture media is collected and the secreted cytokine of the desired type is quantified using Enzyme-Linked Immuno Sorbent Assay ("ELISA") techniques. The use of such tests is well known in the art. One of ordinary skill in the art would recognize that other types of tests are possible.

In an embodiment, the present disclosure provides methods for manufacturing a peritoneal dialysis solution. The method can include any suitable number and type of processing stages. For example, the process can include providing an osmotic agent such as a glucose polymer, contacting the glucose polymer with an enzyme, allowing the enzyme to break down microbial contaminants in the glucose polymer, and using the glucose polymer to make the peritoneal dialysis solution. The glucose polymer can be further processed in any suitable manner. In an embodiment, the glucose polymer can be processed with any suitable number and type of separation devices, such as affinity columns with resins that specifically bind peptidoglycan and/or the like.

The method of manufacturing a dialysis solution in accordance with the present disclosure can also be used in conjunction with other suitable dialysis raw material or dialysis solution testing procedures. Illustrative examples of suitable testing procedures can be found in U.S. Pat. No. 7,118,857, entitled METHODS AND COMPOSITIONS FOR DETECTION OF MICROBIAL CONTAMINANTS IN PERITONEAL DIALYSIS SOLUTIONS, issued on Oct. 10, 2006, the disclosure of which is herein incorporated by reference.

For example, such testing procedures can be generally used to test dialysis raw materials or dialysis solutions.

The dialysis solutions discussed herein may be specifically formulated and suitable for peritoneal dialysis, hemodialysis or any other dialysis therapies. The dialysis solutions can be used, for example, as a single dialysis solution in a single container or as a dialysis part of a separately housed or multi-chambered container. The dialysis solutions can be sterilized using any suitable sterilizing technique such as, for example, autoclave, steam, ultra-violet, high pressure, filtration or combination thereof.

Ready-to-use formulations of dialysis solutions can be prepared in a number of suitable ways. For example, first and second dialysis parts of a multi-part dialysis formulation can be separately stored from each other, such as in separate and hydraulically connected chambers of a multi-chamber container, until mixed together to form a mixed solution. In this regard, the ready-to-use formulation can be prepared within the container by mixing its separate dialysis parts within one chamber of the container. This can effectively eliminate the need to manually inject all or at least a portion of the dialysis parts into the container to form the mixed solution, thus ensuring that the ready-to-use formulation can be readily prepared under sterile conditions.

Further, the container can be configured such that one of the dialysis parts can be placed in direct fluid communication with the patient prior to mixing while the other dialysis part cannot be placed in direct fluid communication with the patient prior to mixing. This can provide an added level of safety with respect to the preparation and administration of the ready-to-use formulation of the present disclosure as the single solution cannot be placed in direct fluid communication with the patient physically and cannot be fed to the patient unless it is first mixed with the other component. In this regard, if, by chance, the single solution that physically cannot be placed in direct fluid communication with the patient were to have an undesirable concentration of constituents, such as potassium, sodium or the like, this configuration would necessarily ensure that the undesirable level of constituents is not fed or administered to the patient.

It should be appreciated that the separate dialysis parts of a multi-part dialysis solution can be housed or contained in any suitable manner such that the individual dialysis parts can be effectively prepared and administered. A variety of containers can be used to house the two parts, such as separate containers (e.g., flasks or bags) that are connected by a suitable fluid communication mechanism. The two or more separate dialysis parts can be separately sterilized and stored.

The dialysis solutions can include one or more suitable dialysis components such as osmotic agents, buffers, electrolytes or combination thereof. A variety of different and suitable acidic and/or basic agents can also be utilized to adjust the pH of the osmotic, buffer and/or electrolyte solutions or concentrates. For example, a variety of inorganic acids and bases can be utilized including hydrochloric acid, sulfuric acid, nitric acid, hydrogen bromide, hydrogen iodide, sodium hydroxide, the like or combination thereof.

Non-limiting examples of osmotic agents include glucose, fructose, glucose polymers (e.g. maltodextrin, icodextrin, cyclodextrins, trehalose), glucose polymer derivatives (e.g. modified starch, hydroxyethyl starch), polyols, amino acids, peptides, proteins, amino sugars, N-acetyl glucosamine (NAG), glycerol and/or the like and combinations thereof. Examples of the buffers include bicarbonate, lactic acid/lactate, pyruvic acid/pyruvate, acetic acid/acetate, citric acid/citrate, amino acids, peptides, an intermediate of the KREBS cycle and/or the like and combinations thereof.

Non-limiting examples of electrolytes include calcium, magnesium, sodium, potassium, chloride and/or the like and combinations thereof. For example, the dialysis solutions can comprise one or more electrolytes in the following ranges from: about 100 to about 140 mEq/L of $Na^+$, about 70 to about 130 mEq/L of $Cl^-$, 0.1 to about 4.0 mEq/L of $Ca^{2+}$, 0.1 to about 4.0 mEq/L of $Mg^{2+}$ and/or 0.1 to about 4.0 mEq/L of $K^+$. Each of these electrolytes can also be absent from the dialysis solution depending on the desired final dialysis formulation.

The osmotic agent can be used to maintain the osmotic pressure of the solution greater than the physiological osmotic pressure (e.g. greater than about 285 mOsmol/kg). For example, glucose is the most commonly used osmotic agent because it provides rapid ultrafiltration rates. Other suitable types of osmotic agents such as amino acids can be used in addition to or as a substitute for glucose.

Another family of compounds capable of serving as osmotic agents in peritoneal dialysis solutions is that of glucose polymers or their derivatives, such as icodextrin, maltodextrins, hydroxyethyl starch, and the like. While these compounds are suitable for use as osmotic agents, they can be sensitive to low and high pH, especially during sterilization and long-term storage. Glucose polymers, such as icodextrin, can be used in addition to or in place of glucose in peritoneal dialysis solutions. In general, icodextrin is a polymer of glucose derived from the hydrolysis of corn starch. It has a molecular weight of 12-20,000 Daltons. The majority of glucose molecules in icodextrin are linearly linked with $\alpha(1-4)$ glucosidic bonds (>90%) while a small fraction (<10%) is linked by $\alpha(1-6)$ bonds.

The dialysis solutions or components can also comprise buffering agents such as bicarbonates and acids. The bicarbonates can comprise an alkaline solution such that the bicarbonate can remain stable without the use of a gas barrier overpouch or the like. The individual bicarbonate solution can have a pH that ranges above about 8.6, preferably about 9. The pH of the bicarbonate solution part can be adjusted with any suitable type of ingredient, such as sodium hydroxide and/or the like. Illustrative examples of the bicarbonate solution of the present disclosure can be found in U.S. Pat. No. 6,309,673, entitled BICARBONATE-BASED SOLUTION IN TWO PARTS FOR PERITONEAL DIALYSIS OR SUBSTITUTION IN CONTINUOUS RENAL REPLACEMENT THERAPY, issued on Oct. 30, 2001, the disclosure of which is herein incorporated by reference.

The acids can include one or more physiological acceptable acids, such as lactic acid, pyruvic acid, acetic acid, citric acid, hydrochloric acid and the like. The acids can be in an individual solution having a pH that ranges from about 5 or less, about 4 or less, about 3 or less, about 2 or less, about 1 or less, and any other suitable acidic pH. The use of an organic acid, such as lactic acid, alone or in combination with another suitable acid, such as a suitable inorganic acid including hydrochloric acid, another suitable organic acid (e.g. lactic acid/lactate, pyruvic acid/pyruvate, acetic acid/acetate, citric acid/citrate) and the like in the acid solution can make the solution more physiologically tolerable.

As discussed previously, the dialysis solutions of the present disclosure can be used in a variety of suitable applications. For example, the dialysis solutions can be used during peritoneal dialysis, such as automated peritoneal dialysis, continuous ambulatory peritoneal dialysis, continuous flow peritoneal dialysis and the like. It should be appreciated that the present disclosure can be used in a variety of different and suitable dialysis therapies to treat kidney failure.

Although the present disclosure, in an embodiment, can be utilized in methods providing a dialysis therapy for patients having chronic kidney failure or disease, it should be appreciated that the present disclosure can be used for acute dialysis needs, for example, in an emergency room setting. Lastly, as one of skill in the art appreciates, the intermittent forms of therapy (e.g., hemofiltration, hemodialysis, peritoneal dialysis and hemodiafiltration) may be used in the in center, self/ limited care as well as the home settings.

Examples

By way of example and not limitation, the following examples are illustrative of various embodiments of the present disclosure and further illustrate experimental testing conducted with dialysis solutions.

Experimental Procedure

The procedure for exposing a sample of dialysis solution to an enzyme was conducted as follows. For Examples 1 and 2 and Comparative Example A, a treatment solution including 1 mg/mL of lysozyme was prepared in water. An 8 mL sample of the dialysis solution was combined with 80 µL of the lysozyme treatment solution. Samples were incubated at 37° C. for 3 hours. Samples were divided into 2×4 mL aliquots, and one of the aliquots was washed extensively in a 30 k membrane to remove the lysozyme, since the non-digested IL-6 inducing material in this solution was known to be retained above the 30 kD membrane. After incubation, the samples were submitted for IL-6 testing.

For Examples 3 and 4 and Comparative Example B, a treatment solution including 1 mg/mL of lysozyme was prepared in 0.9% saline. A 4 mL sample of the solution to be tested was combined with 40 µL lysozyme treatment solution and incubated at 37° C. for 3 hours. After incubation, the samples were submitted for IL-6 testing.

For Examples 5 and 6, icodextrin was dissolved in pyrogen free water to make a 7.5% solution and a treatment solution including 1 mg/mL of lysozyme was prepared in pyrogen free water. A 4 mL sample of the solution to be tested was combined with 40 µL lysozyme treatment solution and incubated at 37° C. for 3 hours. After incubation, the samples were submitted for IL-6 testing.

To determine if a material would induce a cytokine response, a standard interleukin-6 (IL-6) response was performed. Peripheral blood mononuclear cells ("PBMCs") were isolated from four blood donor and used for the testing. A total of four replicates (four wells per sample or control solution) were performed in each experiment with four blood donors. A cell suspension and the solution to be tested articles were mixed together and incubated overnight. After the incubation period the samples were centrifuged and each supernatant was collected. The concentration of IL-6 in the supernatant was determined using the QuantiGlo Chemiluminescent ELISA kit.

To perform the filtration step, AMICON® Ultra-4 filtration devices were used. The AMICON® Ultra-4 devices include membranes made of low-protein binding regenerated cellulose and characterized by an NMWL. The Ultra-4 filtration devices are designed to enable a single spin recovery of the concentrated retentate (collected in the filter unit) and filtrate (collected in the centrifuge tube) that has passed through the filter.

Approximately 4 mL of the test sample was loaded into the filter unit and spun for a pre-determined time so that approximately 2 mL of filtrate was obtained. Both filtrate and retentate were collected and filtered through a 0.2 m syringe filter prior to the PBMC-IL-6 assay. Each sample was separately tested using NMWL filters at 30 kDa.

Results

Example 1 was a peritoneal dialysis solution using icodextrin as an osmotic agent. Example 2 was an icodextrin peritoneal dialysis solution contaminated with microbial products. Comparative Example A was a solution of water with lysozyme.

FIG. 1 illustrates the IL-6 test results for Example 1, Example 2, and Comparative Example A. Comparative Example A, a solution of the lysozyme itself, did not elicit an IL-6 response. Example 1 exhibited a very low response and Example 2 exhibited a strong response. Examples 1 and 2 were then subjected to the lysozyme treatment described above. After the lysozyme treatment, each sample showed very little IL-6 response. Examples 1 and 2 and Comparative Example A were then filtered with 30 kDa NMWL filter and the IL-6 response tested again using the retentate samples from the filters. None of the samples gave a significant IL-6 response. Thus, the treatment with lysozyme was found to digest or break down the microbial contaminants in Example 2. Because the lysozyme did not produce an IL-6 response (Comparative Example A), filtration was not necessary and was not performed in subsequent experiments.

Figure 2:
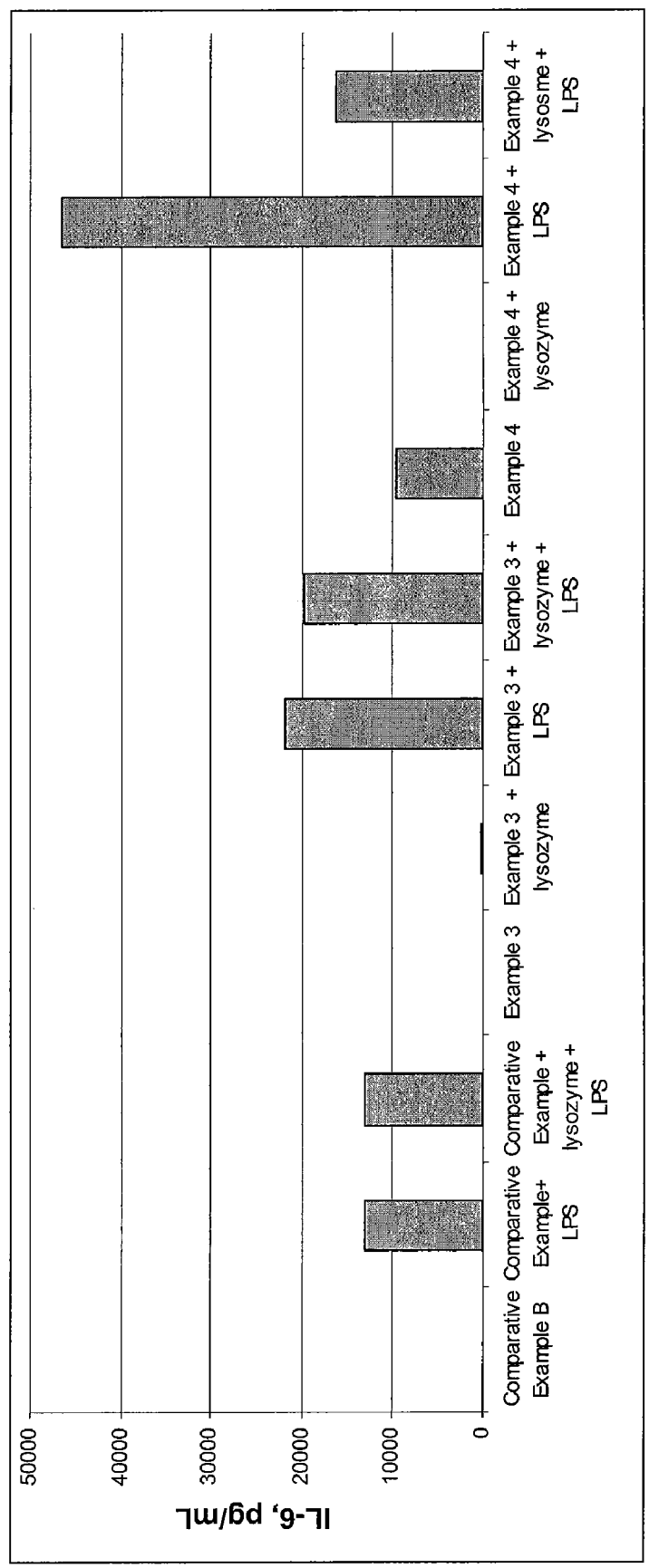
FIG. 2 is a chart illustrating the interleukin-6 response for test samples before and after treating with enzyme and then dosing with lipopolysaccharide.

In a second series of experiments, samples were spiked with lipopolysaccharide ("LPS") after being treated with a lysozyme solution. These tests were conducted to demonstrate that multiple microbial contaminants can produce a synergistic cytokine response and that specific enzymatic treatments can eliminate the synergism, but multiple enzymes may be needed to completely remove all inflammatory microbial contaminants. Example 3 was an icodextrin peritoneal dialysis solution. Example 4 was an icodextrin peritoneal dialysis solution contaminated with microbial products. Comparative Example B was saline solution. For each of Comparative Example B, Example 3, and Example 4, the IL-6 response was measured from samples under the following conditions: 1) sample alone, 2) lysozyme treatment of the sample, 3) LPS addition to the sample, and 4) LPS addition after lysozyme treatment of the sample. The results are illustrated in FIG. 2.

In each case, the addition of LPS after lysozyme treatment of a sample created an IL-6 response reflecting only the LPS addition. For example, the IL-6 response of Comparative Example B with LPS, Comparative Example B with lysozyme and LPS, Example 3 with LPS, Example 3 with lysozyme and LPS, and Example 4 with lysozyme and LPS, all show comparable IL-6 responses. The IL-6 response for Example 4 with LPS is higher due to the original contaminants in the sample in addition to the added LPS. The original contaminants and the LPS are activating the mononuclear cells through two separate Toll-Like Receptors (such as TLR4 for LPS and TLR2 for peptidoglycan) inducing a synergistically elevated response. Destroying the microbial contaminant in Example 4 before addition of the LPS results in a response consistent with only LPS stimulation of TLR4.

In a third set of experiments a raw material that is used as a component of a dialysis solution, icodextrin, was tested in an IL-6 assay before lysozyme treatment and after lysozyme treatment. Example 5 was a raw material contaminated with microbial products and Example 6 was a raw material uncontaminated with microbial products. FIG. 3 illustrates the test results as follows: Example 5 exhibits a strong IL-6 response, Example 5 after lysozyme treatment shows a low response, Example 6 shows a low response, and Example 6 after lysozyme treatment shows a low response. Example 6 shows the same response before treatment as after treatment, thus showing that Example 6 is uncontaminated. Example 5 after lysozyme treatment shows an IL-6 response comparable to Example 6 both before and after lysozyme treatment, thus showing that the microbial contaminants in Example 5 were destroyed.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method of treating a dialysis component, the method comprising:
   providing a dialysis component for peritoneal dialysis;
   contacting the dialysis component with an enzyme selected from the group consisting of N-acetylmuramyl-L-alanine amidase, lysozyme, amidases, trypsins, chitinases, beta 1-3 glucanases, pronases, proteases, lipases, endoglycosidases and combinations thereof;
   allowing the enzyme to break down microbial contaminants in the dialysis component; and
   separating the enzyme from the dialysis component to provide a purified dialysis component.

2. The method of claim 1, wherein the purified dialysis component is substantially free of microbial contaminants that cause a cytokine response in humans.

3. The method of claim 1, wherein the enzyme is added at a ratio of between about 0.0005% and about 0.05% by weight of the dialysis component.

4. The method of claim 1, wherein the dialysis component is selected from the group consisting of glucose polymers, hydroxyethyl starch, modified starch and combinations thereof.

5. The method of claim 1 further comprising incubating the dialysis component and the enzyme for a period of time.

6. The method of claim 5, wherein the period of time is at least 1 hour.

7. The method of claim 1, wherein the step of contacting the dialysis component with an enzyme comprises adding to the dialysis component a treatment solution comprising the enzyme.

8. The method of claim 7, wherein the step of separating the enzyme from the dialysis component comprises filtering the enzyme from the dialysis component.

9. The method of claim 8, wherein the enzyme is naturally larger than the molecular weight cut off of the filter.

10. The method of claim 1, wherein the enzyme is fixed to a substrate.

11. The method of claim 10, wherein the substrate is a bead or a membrane.

12. The method of claim 1, wherein the step of contacting the dialysis component with an enzyme is performed in a batch process.

13. The method of claim 1, wherein the step of contacting the dialysis component with an enzyme is performed in a continuous process.

14. The method of claim 1 further comprising the step of testing the dialysis component for the presence of microbial contaminants after the step of allowing the enzyme to break down microbial contaminants in the dialysis component.

15. The method of claim 14, where the testing is interleukin-6 testing.

16. The method of claim 1, wherein the dialysis component includes peptidoglycan as a microbial contaminant.

17. The method of claim 1, wherein the dialysis component is icodextrin.

18. A method of treating a peritoneal dialysis solution, the method comprising:
   providing a peritoneal dialysis solution comprising a glucose polymer, hydroxyethyl starch or modified starch;
   contacting the peritoneal dialysis solution with an enzyme selected from the group consisting of N-acetylmuramyl-L-alanine amidase, lysozyme, amidases, trypsins, chitinases, beta 1-3 glucanases, pronases, proteases, lipases, endoglycosidases and combinations thereof;
   allowing the enzyme to break down microbial contaminants in the peritoneal dialysis solution; and
   separating the enzyme from the peritoneal dialysis solution to provide a purified peritoneal dialysis solution.

19. The method of claim 18, wherein the step of contacting the peritoneal dialysis solution with an enzyme comprises adding to the peritoneal dialysis solution a treatment solution comprising the enzyme.

20. The method of claim 18, wherein the step of separating the enzyme from the peritoneal dialysis solution comprises filtering the enzyme from the peritoneal dialysis solution.

21. A method of providing peritoneal dialysis to a patient, the method comprising:
   providing a peritoneal dialysis component comprising a glucose polymer, hydroxyethyl starch or modified starch;
   contacting the peritoneal dialysis component with an enzyme selected from the group consisting of N-acetylmuramyl-L-alanine amidase, lysozyme, amidases, trypsins, chitinases, beta 1-3 glucanases, pronases, proteases, lipases, endoglycosidases and combinations thereof;
   allowing the enzyme to break down microbial contaminants in the peritoneal dialysis component;
   separating the enzyme from the peritoneal dialysis component to provide a purified peritoneal dialysis component;
   using the purified peritoneal dialysis component to make a peritoneal dialysis solution; and
   using the peritoneal dialysis solution in a treatment of a patient.

* * * * *